United States Patent [19]

Wimmer

[11] Patent Number: 5,662,677

[45] Date of Patent: Sep. 2, 1997

[54] CUPPING INSTRUMENT FOR A CUPPING TREATMENT OF SKIN AND BODY PORTIONS

[76] Inventor: Erwin Wimmer, Thurnsdorf 3, A-4300 St. Valentin, Austria

[21] Appl. No.: 560,998

[22] Filed: Nov. 21, 1995

[30] Foreign Application Priority Data

Jan. 4, 1995 [AT] Austria ................. A 10/95

[51] Int. Cl.$^6$ ............................................. A61B 17/00
[52] U.S. Cl. ......................... 606/201; 604/313; 604/316
[58] Field of Search ........................... 606/201; 604/73, 604/74, 313, 314, 315, 316

[56] References Cited

U.S. PATENT DOCUMENTS 4,287,819  9/1981  Emerit ........................... 604/316

FOREIGN PATENT DOCUMENTS

| 98007 | 4/1924 | Austria . | |
|---|---|---|---|
| 619574 | 4/1927 | France | 604/313 |
| 746185 | 5/1933 | France | 604/313 |
| 807003 | 12/1936 | France . | |
| 865309 | 5/1941 | France | 604/313 |
| 895006 | 1/1945 | France . | |
| 930044 | 1/1948 | France . | |
| 971276 | 1/1951 | France . | |
| 856788 | 11/1952 | Germany | 604/313 |

*Primary Examiner*—Michael Buiz
*Assistant Examiner*—Patrick W. Rasche
*Attorney, Agent, or Firm*—Collard & Roe, P.C.

[57] ABSTRACT

A cupping instrument comprises a vacuum cup integrally comprising an outlet hole at one end thereof, an annular socket concentrically surrounding the outlet hole, and a cylindrical tubular extension extending from the one end and surrounding the outlet hole and the annular socket. A suction valve for opening and closing the outlet hole is disposed in the annular socket and comprises a sealing disk, a centrally disposed die-cut valve disk, an annular outer portion surrounding the valve disk, and at least one bridge integrally connecting the annular outer portion to the valve disk. An aspirator is connected to the vacuum cup, the aspirator comprising an aspirator cylinder detachably mounted in the cylindrical tubular extension and having a forward end wall facing the outlet hole and defining an aspirating opening concentrically surrounding the outlet hole. The annular socket has an outside diameter which is larger than the diameter of the aspirating opening, and an aspirating piston is slidably mounted in the aspirator cylinder and comprises a piston skirt having an extended end remote from the piston head to form a handle protruding out of the cylinder.

5 Claims, 2 Drawing Sheets

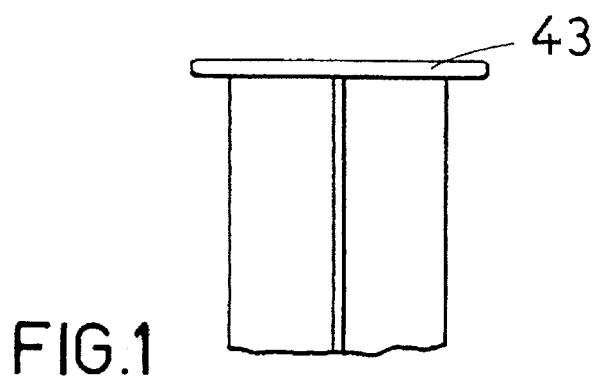
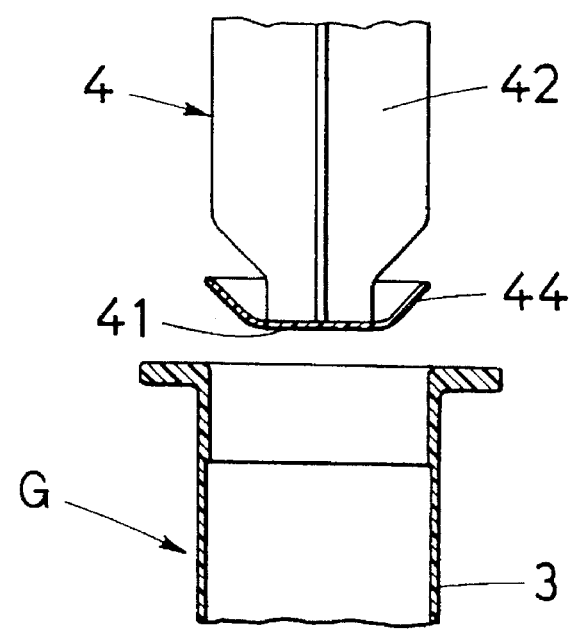
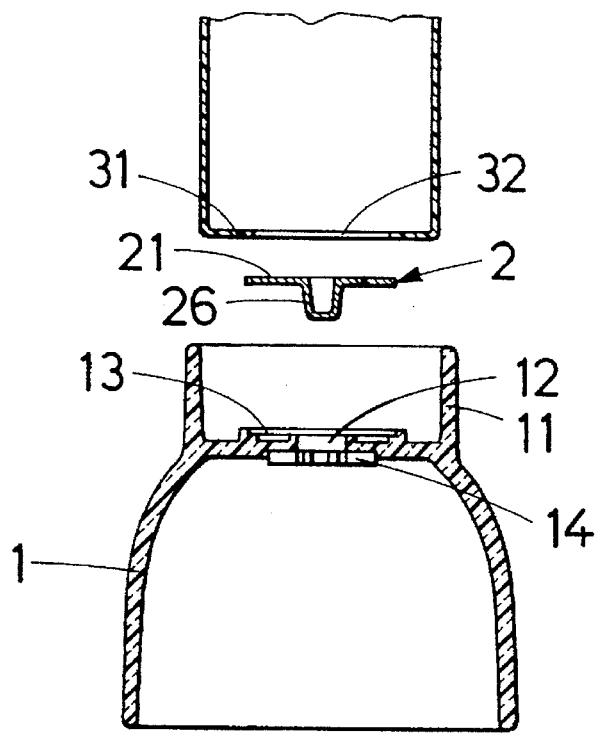
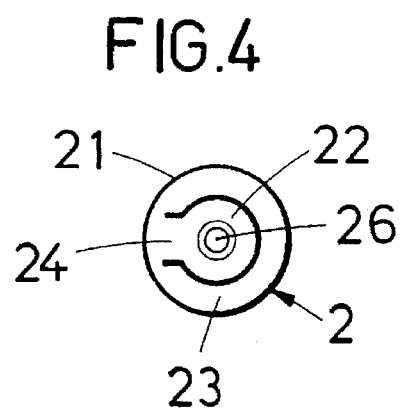
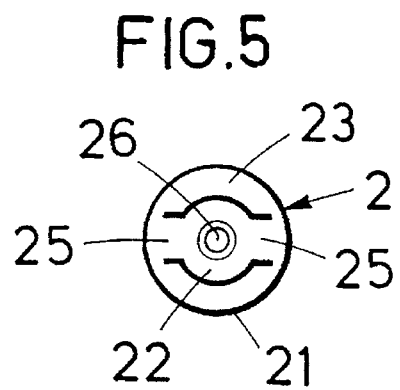
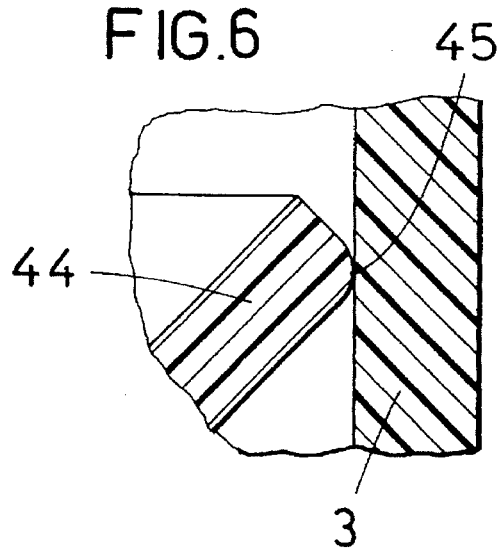

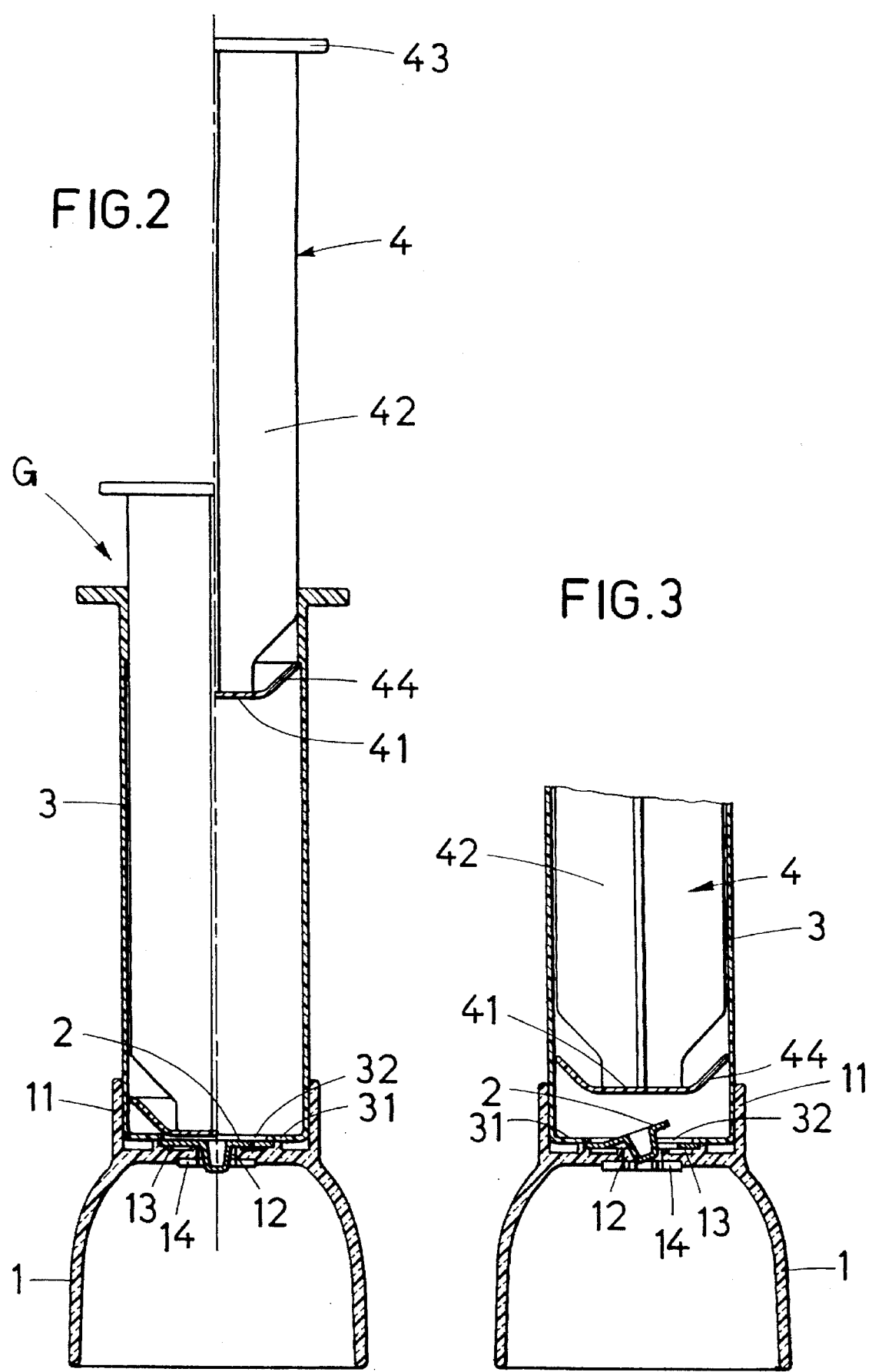

CUPPING INSTRUMENT FOR A CUPPING TREATMENT OF SKIN AND BODY PORTIONS

BACKGROUND OF THE INVENTION

1. Field of the Invention

This invention relates to a cupping instrument for a cupping treatment of skin or body portions, comprising a vacuum cup and an aspirator, which is detachably connected to said vacuum cup, wherein the vacuum cup comprises an outlet hole and adjacent to said outlet hole is provided with a suction valve, and the aspirator comprises an aspirating cylinder and an aspirating piston, which is slidably mounted within the aspirating cylinder, the aspirating cylinder is formed in its forward end wall with an aspirating opening, which is coaxial to said outlet hole, and the aspirating piston comprises a piston head and on that side of said piston head which faces away from said aspirating opening comprises a piston skirt, which is extended to form a handle that protrudes from said aspirating cylinder.

2. Description of the Prior Art

For cupping, a portion of the skin is subjected to a vacuum. Cupping treatments are often performed to stimulate blood vessels, lymphatic vessels, connective tissue, and muscles in order to exert a favorable influence on the circulation of the blood and lymph. The vacuum which is locally exerted results in a short-time expansion of the capillaries, which constitute the smallest blood vessels, so that the flow of blood into the hypodermis is increased and the entire cellular and intermediate metabolism is promoted.

Such a cupping treatment has previously been performed often by means of cupping heads, which consist of vacuum cups of glass and which before they are applied to the skin are evacuated in that cotton wool is combusted within the cup. The manipulation of such vacuum cups is difficult and they can hardly be used to exert a controlled vacuum on the skin and are liable to give rise to burns whenever they are used.

In other known cupping instruments disclosed in AT-B 98,007 and FR-A 895 006 the vacuum cups have an outlet hole which is adapted to be opened and closed by a valve and to which an aspirator consisting of a piston-cylinder unit can be connected. But that aspirator is held against the cup only in order to evacuate the latter so that a complicated manipulation is required and the effect of the treatment can hardly be controlled. Besides, the permanently installed suction valves and the aspirating cylinders, which are provided with separate sealing rings or sealing sleeves for connection to the vacuum cup, are rather expensive and can be kept clean only with difficulty.

SUMMARY OF THE INVENTION

It is an object of the invention to eliminate the disadvantages outlined hereinbefore and to provide a cupping instrument which is of the kind described first hereinbefore and can be manufactured in a simple manner, can easily be operated, can be used to exert a controlled vacuum, and, above all, can satisfactorily be cleaned.

That object is accomplished in accordance with the invention in that the outlet hole is disposed within a rearwardly extending cylindrical tubular extension provided at the rear end of the vacuum cup, that the suction cylinder is detachably mounted in the cylindrical extension adjacent to the outlet hole, that the outlet hole is concentrically surrounded by an annular socket, which has an outside diameter that is larger than the diameter of said aspirating opening, and that the annular socket contains a suction valve consisting of a sealing disc, which comprises a centrally disposed, die-cut valve disk, which is smaller in diameter than the aspirating opening and larger in diameter than said outlet hole, and the valve disk and the outer annular portion of the sealing disk are integrally connected by at least one bridge.

It is apparent that said cupping instrument essentially consists of a combination of a suction bell and a modified syringe, which instead of a needle holder is provided with an aspirating opening and to which instead of the needle the vacuum cup is attached with a suction valve interposed. Those components can economically be manufactured from the materials which are most desirable for said components. For instance, the vacuum cup may be made of transparent plastic, such as polymethyl methacrylate (PMMA); the suction valve may be made of rubber or a rubberlike material; and the aspirating cylinder and the aspirating piston may be made of a synthetic thermoplastic, such as polypropylene or polyethylene. The components can be assembled by a few manual operations without the need for a tool in that the parts are simply interfitted or screwed together. The suction valve consists only of a sealing disk, the central portion of which constitutes a valve disk. Said sealing disk is clamped in position in the annular socket between the vacuum cup and the aspirating cylinder. The relative dimensions of the outlet hole, aspirating opening, and valve disk are so selected that the desired functions of the valve will reliably be performed if the valve disk is lifted from and forced against the outlet hole. If the valve disk is connected to the outer annular portion of the sealing disk by only one bridge, the valve will function like a flap valve. If there are two or more connecting bridges, the valve will function like a diaphragm valve. The function and design of the valve will be selected in each case in dependence on the material of the valve and on the method by which it is manufactured. Because the instrument can be taken apart into its individual components, it can be thoroughly be cleaned within a short time. The operation of the instrument is simple because it comprises a syringelike aspirator, which remains attached to the vacuum cup during the treatment. The selection of the suction stroke permits an effective control of the vacuum which is exerted. Because the maximum evacuation is effected by a complete piston stroke permits an effective control of the vacuum which is exerted. Because the maximum evacuation is effected by a complete piston stroke, the exertion of an excessive vacuum need not be feared. The cupping instrument can be used without a need for any additional implement or accessory. It can be operated quickly and in a simple manner, and the vacuum Exerted by it can be selected for different kinds of treatment and in adaptation to the sensitivity of the skin portion which is to be treated. Because the vacuum which is exerted can effectively be controlled, the instrument can be operated at a fixed location on the skin or be shifted on the skin during the treatment.

If the valve disk comprises a boss, which extends through the outlet hole, the valve disk will be centered and it will be possible to open the suction valve in that pressure is applied to the boss by a finger inserted through the vacuum cup in order to prepare the aspirator for the cupping operation in that the piston is advanced within the aspirating cylinder. In that case the vacuum cup may be integrally formed on its inside surface adjacent to the outlet hole with angularly spaced apart radial lugs so that the opening of the suction valve will be further simplified and it will be ensured that the finger which raises the boss will not close the outlet hole but a continued flow of air will be permitted through the slots left between the radial lugs.

Different vacuum cups having identical cylindrical extensions may be combined in a kit with a given aspirating cylinder to permit the use of a vacuum cup which is suitable for a given desired cupping treatment. The skin area on which a vacuum is exerted will mainly be determined by the size of the opening of the cup at its end that is opposite to the outlet hole so that a controlled cupping action can be performed.

The aspirating cylinder may be connected to the cylindrical extension by mating screw threads or by a bayonet joint or may merely slidably be fitted in the cylindrical extension. If the aspirating cylinder is merely slidably fitted in the cylindrical extension, a firmer clamping action and a tighter seal may be ensured in that the cylindrical extension has a slightly tapered conical inside surface and the aspirating cylinder has a forward portion which is inserted into the cylindrical extension and has a conical outside surface mating said conical inside surface of the cylindrical extension. In that case the aspirating cylinder and the cylindrical extension will firmly and tightly interfit even if said conical surfaces are smooth. Said conical surfaces desirably have an included angle of a few degrees, such as 1 to 3 degrees.

BRIEF DESCRIPTION OF THE DRAWING

FIG. 1 is an exploded view showing a cupping instrument in accordance with the invention with components shown in section.

FIG. 2 is an axial sectional view showing the assembled cupping instrument in two operative positions.

FIG. 3 is a fragmentary axial sectional view showing a part of the cupping instrument in cupping position.

FIGS. 4 and 5 are top plan views showing two illustrative embodiments of the suction valve.

FIG. 6 is a sectional view showing a detail of the aspirating piston on a larger scale.

DETAILED DESCRIPTION OF THE PREFERRED EMBODIMENTS

Illustrative embodiments of the invention will now be described in more detail with reference to the drawing.

A cupping instrument G for a cupping treatment of skin and body portions comprises a vacuum cup 1, a suction valve 2, and an aspirator comprising an aspirating cylinder 3 and an aspirating piston 4. The vacuum cup 1 is made of transparent material and at its rear end comprises a cylindrical extension 11, which surrounds a centrally disposed outlet hole 12 in an annular socket 13 that contains the suction valve 2. Adjacent to the outlet hole 12 the vacuum cup 1 is integrally formed on its inside surface with angularly spaced apart radial lugs 14 so that the outlet hole 12 cannot be closed on the side facing the interior of the vacuum cup.

The suction valve 2 consists of a sealing disk 21, which is made of rubber or a rubberlike material and which comprises a centrally disposed die-cut valve disk 22. The valve disk 22 and the outer annular portion 23 of the sealing disk 21 are integrally connected by one connecting bridge 24 (FIG. 4) or by two diametrically opposite connecting bridges 25 (FIG. 5). The valve disk 22 is integrally formed with a boss 26, which protrudes through the outlet hole 12 into the interior of the vacuum cup.

The aspirating cylinder 3 is made of a synthetic thermoplastic material and has a flat forward end wall 31 that is formed with an aspirating opening 32. An aspirating piston 4 is slidably mounted within the aspirating cylinder 3 and is also made of a synthetic thermoplastic material and comprises a piston head 41, which faces the aspirating opening 32, and a piston skirt 42, which comprises a handle 3, which protrudes from the aspirating cylinder 3 at its rear end. The piston head 41 of the aspirating piston 4 comprises a centrally disposed flat end wall and a conical annular flange 44, which flares toward the rear and is formed with a convexly curved sealing edge portion 45 (FIG. 6).

The cupping instrument G can be assembled in a simple manner. After the sealing disk 2 has been inserted into the annular socket 13 of the vacuum cup 1, the aspirating cylinder 3 is inserted into the cylindrical extension of the vacuum cup 1. The aspirating piston 4 may be inserted into the cylinder 3 before or after the latter has been inserted. To force the piston 4 to its initial position for the cupping treatment, the suction valve is opened in that the boss 26 is raised from the interior of the vacuum cup to lift the valve disk 22 from the vacuum cup 1 and the piston 4 is then advanced until it engages the forward end wall 31 of the cylinder (as is shown on the left in FIG. 2). The vacuum cup 1 may now be applied to the skin portion which is to be treated and can be evacuated in that the piston 4 is pulled out of the aspirating cylinder 3. During the suction stroke of the piston 4 the valve disk 22 is lifted from the outlet hole 42 so that air is sucked out of the vacuum cup (FIG. 3). The vacuum which is thus created within the vacuum cup 1 will depend on the length of the suction stroke of the aspirating piston 4 and can be controlled in a simple manner. The position of the piston during or after its suction stroke can be indicated, e.g., by marks provided on the aspirating cylinder 3 or on the piston skirt of the aspirating piston. As soon as the piston has reached the desired position at the end of the suction stroke, the piston is released and the pressure difference between the interior of the vacuum cup and the interior of the aspirating cylinder then causes the suction valve 2 to close so that a vacuum is exerted on the skin portion which faces the interior of the vacuum cup 1, as is shown on the right in FIG. 2.

In order to admit air to the interior of the vacuum cup 1, it will be sufficient to depress a skin portion at the rim of the vacuum cup 1 so that the vacuum cup 1 is no longer in tight contact with the skin and the cupping instrument can be removed from the skin after air has flown into the vacuum cup 1.

I claim:

1. A cupping instrument for a cupping treatment of skin and body portions, comprising
   (a) a vacuum cup integrally comprising
      (1) an end wall defining an outlet hole,
      (2) an annular socket on the end wall concentrically surrounding the outlet hole, and
      (3) a cylindrical tubular extension extending from the end wall and surrounding the outlet hole and the annular socket,
   (b) a suction valve for opening and closing the outlet hole, the suction valve being disposed in the annular socket and comprising
      (1) a sealing disk,
      (2) a centrally disposed die-cut valve disk,
      (3) an annular outer portion surrounding the valve disk, and
      (4) at least one bridge integrally connecting the annular outer portion to the valve disk, and
   (c) an aspirator connected to the vacuum cup, the aspirator comprising (1) an aspirator cylinder detachably mounted in the cylindrical tubular extension and having a forward end wall facing the outlet hole and defining an aspirating opening concentrically surrounding the outlet hole, the outlet hole being smaller in diameter than the aspirating opening, the annular socket having an outside diameter which is larger than the diameter of the aspirating opening, and the valve disk being smaller in diameter than the aspirating opening and larger in diameter than the outlet hole, the aspirating opening being adapted to communicate with the outlet hole through the suction valve, and (2) an aspirating piston slidably mounted in the aspirator cylinder and comprising a piston head facing the forward end wall and a piston skirt having an extended end remote from the piston head to form a handle protruding out of the cylinder.

2. The cupping instrument set forth in claim 1, wherein said valve disk extends between said outlet hole and said aspirating opening and comprises a boss, extending through said outlet hole into the interior of said vacuum cup.

3. The cupping instrument set forth in claim 1, wherein angularly spaced apart radial lugs are integrally formed with said vacuum cup on its inside surface adjacent to said outlet hole.

4. The cupping instrument set forth in claim 1, wherein said vacuum cup is one of a set of different ones of such vacuum cups which have identical cylindrical extensions.

5. The cupping instrument set forth in claim 4, wherein said vacuum cups, at their end that is opposite to said outlet hole have openings which differ in size for exerting a vacuum on skin portions differing in size.

* * * * *